Figure 1:
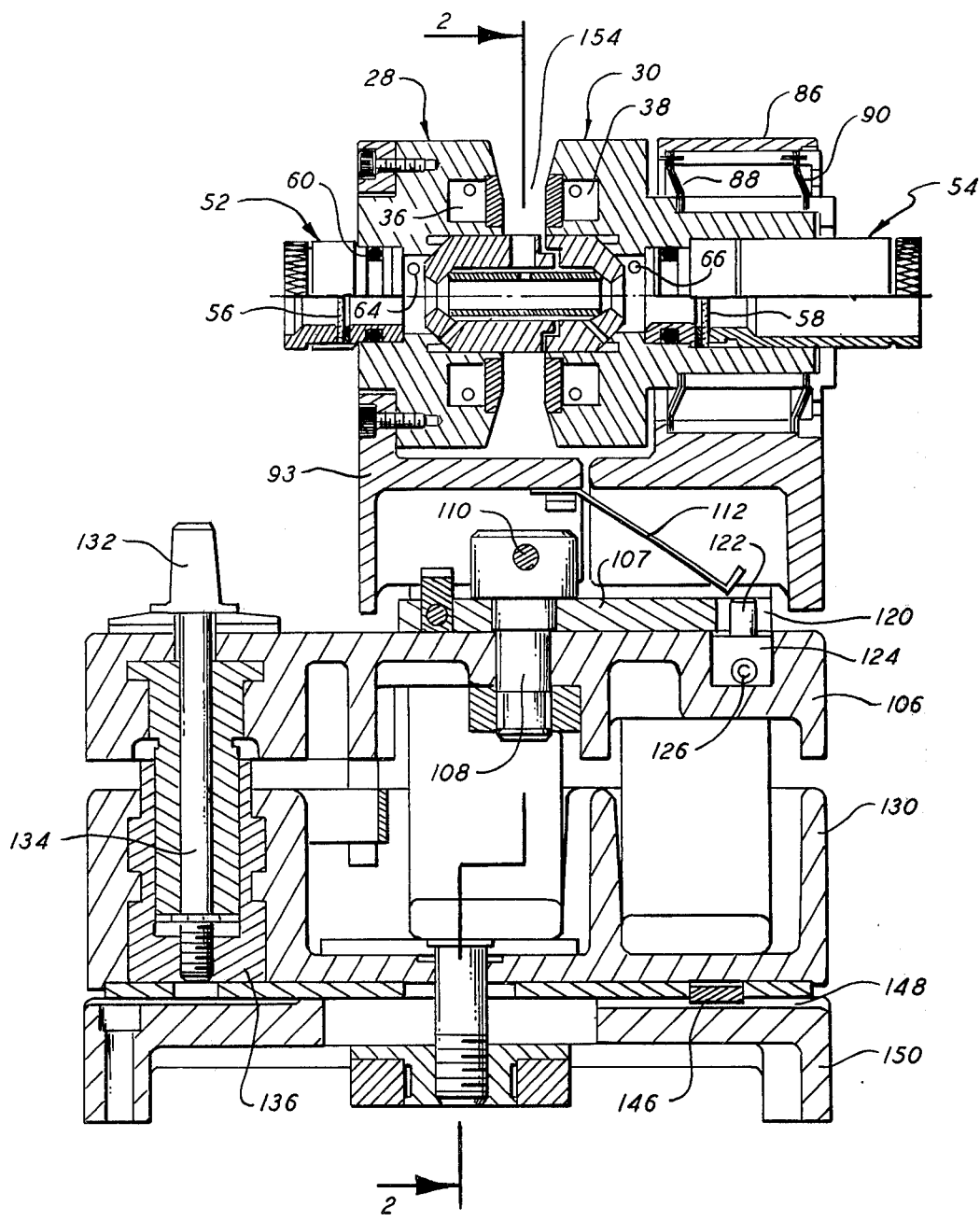
Figure 1A:
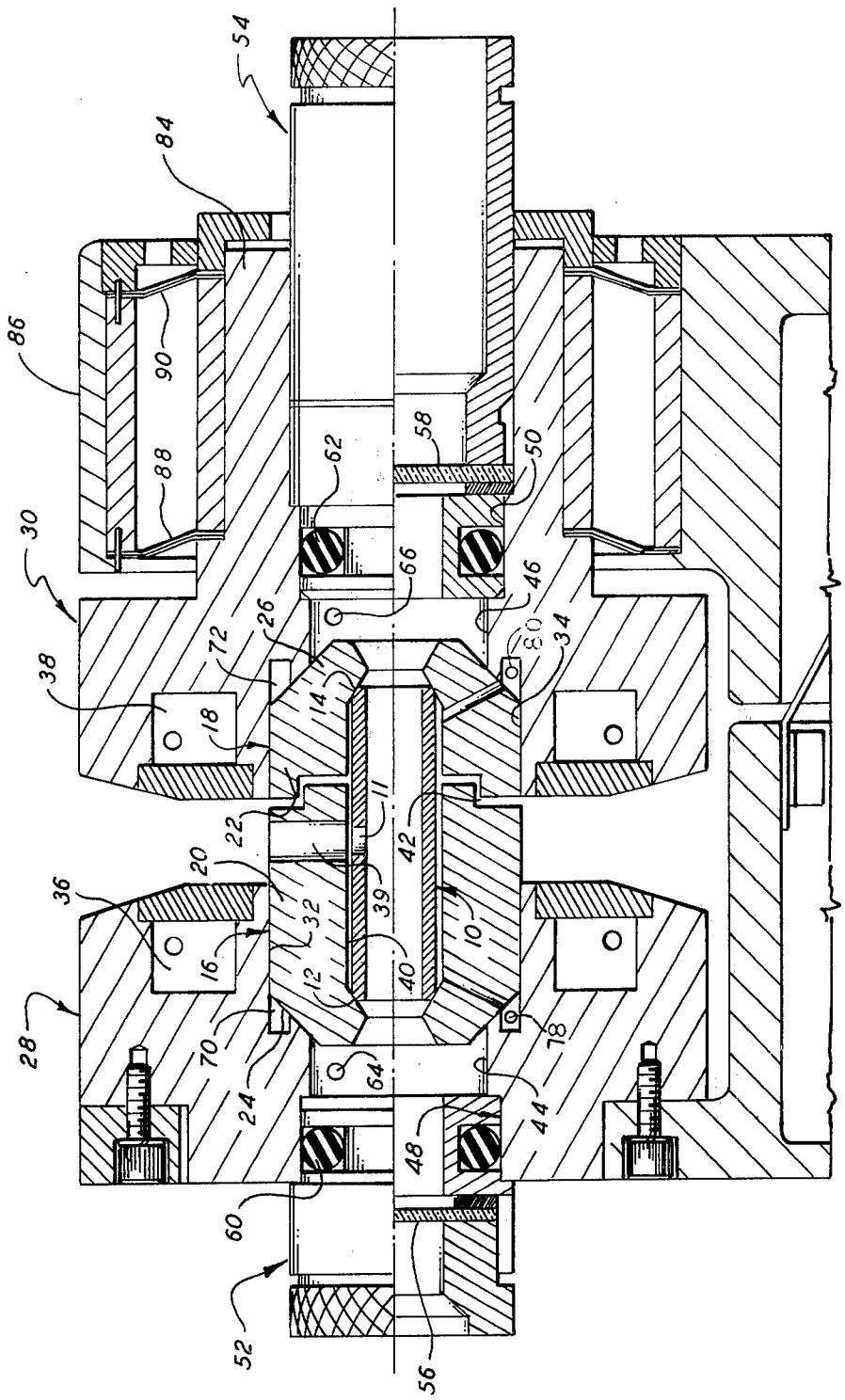

United States Patent [19]

Braun et al.

[11] 4,022,530
[45] May 10, 1977

[54] DEVICE FOR ATOMIZING A SAMPLE FOR FLAMELESS ATOMIC ABSORPTION MEASUREMENTS

[75] Inventors: Klaus Braun; Wolfgang Chlosta; Franz Eier; Bernhard Werner Huber, all of Uberlingen; Rolf Günther Arnold Tamm, Salem, all of Germany

[73] Assignee: Bodenseewerk Perkin-Elmer & Co. GmbH, Uberlingen, Germany

[22] Filed: Aug. 28, 1975

[21] Appl. No.: 608,558

Related U.S. Application Data

[63] Continuation of Ser. No. 561,286, March 24, 1975, abandoned.

[30] Foreign Application Priority Data

Mar. 22, 1974 Germany .......................... 2413782

[52] U.S. Cl. .............................. 356/85; 356/244 V
[51] Int. Cl.² ...................... G01N 21/16; G01J 3/30
[58] Field of Search .............................. 356/85, 244

[56] References Cited

UNITED STATES PATENTS

| | | | |
|---|---|---|---|
| 3,788,752 | 1/1974 | Slavin | 356/244 |
| 3,817,629 | 6/1974 | Witte | 356/244 |

*Primary Examiner*—Vincent P. McGraw
*Attorney, Agent, or Firm*—S. A. Giarratana; F. L. Masselle; J. M. O'Meara

[57] ABSTRACT

A graphite furnace for flameless atomic absorption spectroscopy comprising a graphite sample tube with a sample port at the mid-point of its length. Electrodes supportively contact the tube ends and pass electrical heating current through the tube. The electrodes have hollow cylindrical portions which laterally envelope the tube over substantially its entire length, one of the electrodes being longer than the other and containing a radial bore in registration with the sample port. The cylindrical portions of the electrodes are disposed with complementary-shaped recesses in cooling jackets which encase all but the mid-length regions of the electrode cylindrical portions. The electrodes fit readily in the cooling jackets at room temperature due to differential expansion of these members. The sample tube, electrodes, cooling jackets and associated structure are mounted on a base with provisions for adjustment of the tube about various orthogonal axes.

23 Claims, 10 Drawing Figures

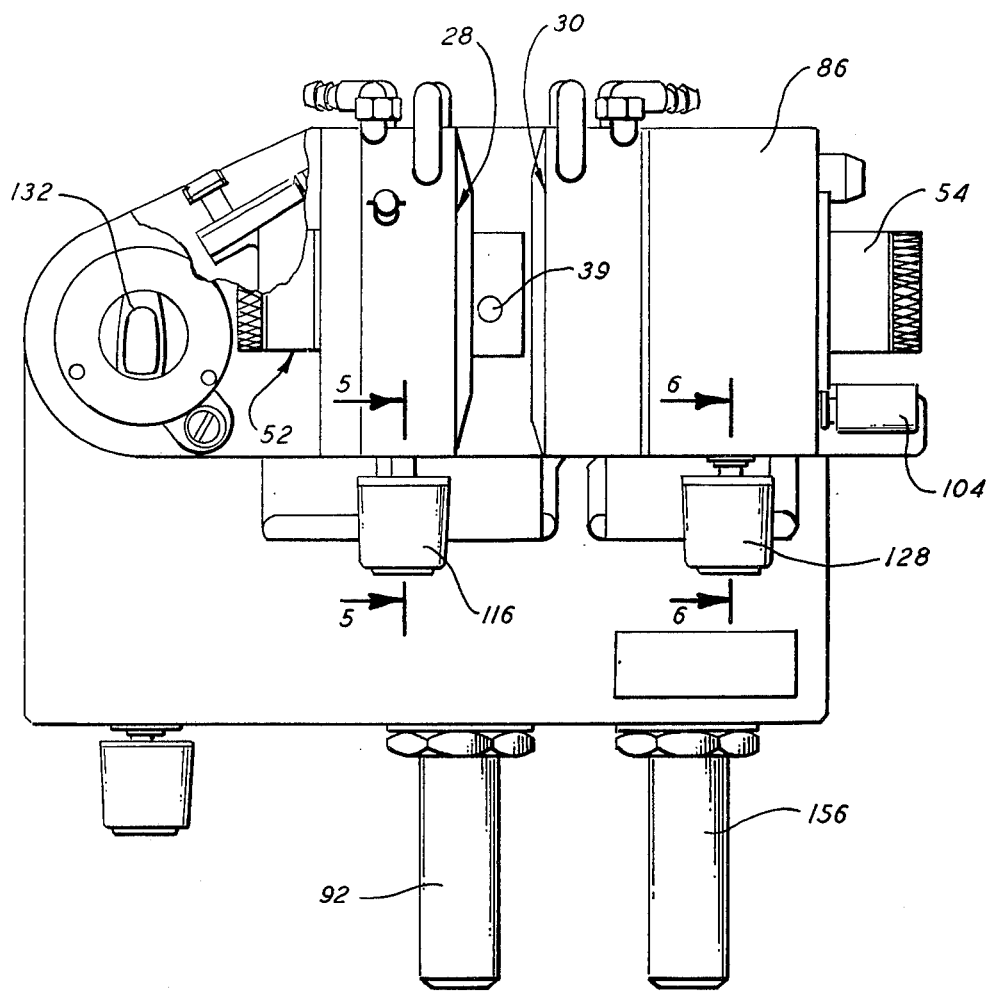
FIG. 4
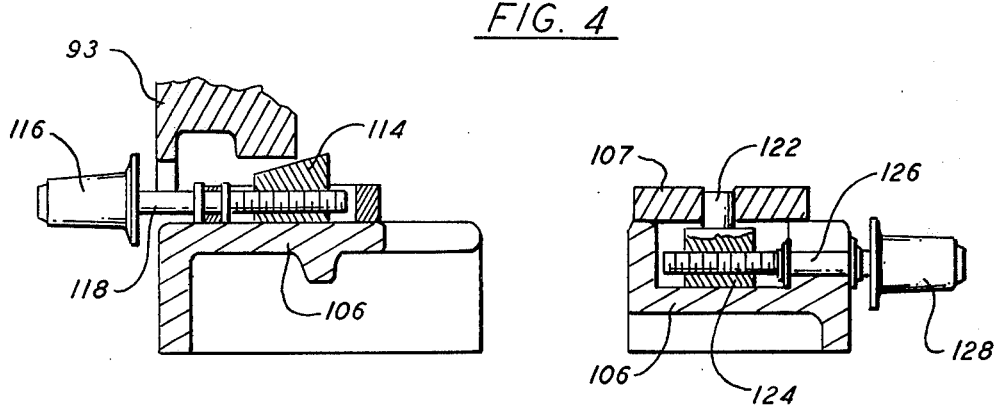
FIG. 5
FIG. 6

DEVICE FOR ATOMIZING A SAMPLE FOR FLAMELESS ATOMIC ABSORPTION MEASUREMENTS

This application is a continuation of Ser. No. 561,286 filed Mar. 24, 1975, now abandoned.

BACKGROUND OF THE INVENTION

1. Field of the Invention

This invention relates to apparatus for flameless atomization of a sample for atomic absorption analysis and, more particularly, to such an apparatus which comprises a tubular body in which the sample is contained and heated by means of an electric current passed through the body. Such apparatus are commonly referred to as "graphite furnaces" with allusion to the fact that the tubular body, hereinafter frequently called the sample tube, is normally fabricated of graphite.

2. Summary of the Prior Art

Apparatus of the type to which the invention relates customarily employ a cylindrical graphite sample tube having a radial bore at substantially the midpoint of its length, the bore providing a port through which the sample may be introduced into the tube. The electrical heating current is passed through the tube by means of respective, generally annular, electrodes, typically also of graphite, in pressure contact with, and supporting, the tube ends. The annular configuration of the electrodes permits a beam of radiation, of selected spectral characteristics, to be directed through the tube to effect analysis of the atomized sample in a manner well known in the art of atomic absorption spectroscopy. In this connection, reference may be had to U.S. Pat. No. 2,847,899. Normally, atomization of the sample requires heating of the tube (usually performed in stages to effect drying and ashing of the sample preparatory to its atomization) to extremely high temperatures; consequently, cooling jackets of high thermal conductivity material are provided for the electrodes and the tube is enveloped in a mantle of flowing protective gas to prevent its combustion. This requires defining an annular chamber for the gas surrounding the tube while still enabling access to the sample port.

In prior art, graphite furnaces of the type described in U.S. Pat. No. 3,778,156, the sample tube is surrounded for the greater part of its length directly by the cooling jackets, the proximal ends of which have axial collars overlapping so as to form an annular axial gap. The cooling jackets, in turn, are enclosed by a cylindrical housing forming an annular space surrounding the proximal ends of the cooling jackets. Protective gas introduced into this annular space flows through the annular axial gap between the cooling jacket collars into an annular space between the cooling jackets and graphite tube and from there through the sample port into the interior of the graphite tube. Such a structure does not provide ready accessibility of the sample port although one sample tube known in the prior art has an inspection arrangement, designed in the manner of a pinhole camera, screwed into the housing in alignment with the sample port of the graphite tube. This observing arrangement can be unscrewed so that a relatively large diameter opening remains in the housing through which the sample port of the graphite tube is accessible. Thus, it is possible to guide a pipette through the opening of the housing to the sample port in order to introduce the sample. Handling, however, is painstaking and difficult since sample injection requires unscrewing of the observing arrangement and the radial distance between the sample port and the opening in the housing is quite large.

It is also known in the prior art to provide a slide closure member in the housing between the cooling jackets, by which a housing opening is optionally exposed or covered. Such an arrangement also requires separate opening and closing actions when introducing the sample and creates the need to ensure that the opening is closed during heating of the tube. Moreover, in this case also, the radial distance between the housing opening and the sample port in the graphite tube is undesirably great thus complicating the injection of the sample (by means of a pipette, for example).

Another shortcoming of prior art graphite furnaces in which the sample tube is substantially surrounded by the metallic cooling jackets is the fact that undesired temperature changes sometimes occur in the sample tube even though the heating current is maintained at a constant level, for the following reason.

As long as the cooling jacket parts facing the sample tube are bare, they reflect the heat radiated outwardly by the heated graphite tube. However, in the course of operation, the bare cooling jacket parts become coated with graphite dust originating from the hot graphite tube so that an increasing portion of the radiant heat energy emitted by the sample tube is absorbed and carried off by the coolant flowing through cooling jackets. Therefore, when the surfaces of the cooling jackets are bare, the temperature of the sample tube at a given current level is greater than when the surfaces are blackened by graphite dust. In the prior graphite furnaces, the temperature of the sample tube also depends on the temperature of the cooling jackets and thus, for instance, on the intensity of cooling.

In the graphite furnace shown in the aforementioned U.S. Pat. No. 3,778,156, an inert gas stream enters through the sample port in the mid-length region of the graphite tube and from there flows to both ends of the graphite tube. In the vicinity of the ends of the tube, there are provided further radial bores. A protective gas stream flowing over the exterior of the graphite tube enters the graphite tube through these radial bores thus precluding admission of air which would result in conbustion of the tube at high operating temperatures. These protective gas streams also flush the atomized sample from the graphite tube, the vapors passing over the surface of the electrodes and the exposed portions of the contact surfaces by which cooling jackets abut the electrodes. The atomized sample may contain corrosive vapors which attack exposed metallic surfaces in particular the cooling jacket surfaces.

In a co-pending U.S. patent application Ser. No. 453,114 filed Mar. 20, 1974 and assigned to the same assignee as the present invention, there is disclosed a graphite furnace in which a protective gas stream flows from the ends of the sample tube inwardly and exits through the sample port. The graphite tube is surrounded by an annular protective gas chamber defined by a cylindrical outer housing wall, cooling jackets, the inner end surfaces of the electrodes and the cylindrical outer surface of the graphite tube; this chamber is in communication with the sample port and is connected with a protective gas outlet. In such a furnace, an additional protective gas stream can be introduced into the annular chamber via a protective gas inlet formed by a nipple extending radially through the housing wall and into the annular chamber terminating the close proximity to the sample port. This arrangement prevents the atomized sample from emerging through the sample port and passing into the annular chamber to form deposits there at the cool wall portions, in particular, the cooling jackets. Injection of the sample is effective either via this nipple or by way of an annular slide closure rotatable with the nipple to expose an opening in the housing.

SUMMARY OF THE INVENTION

It is the basic general object of the present invention to provide a novel graphite furnace for flame atomic absorption spectroscopy which overcomes or at least mitigates one or more of the problems of the prior art as outlined above.

A more specific object is the provision of an improved graphite furnace having cooling jackets which are shielded for the sample tube.

Another object is the provision of a novel graphite furnace which enables quick, easy and convenient introduction of the sample into the sample tube.

A further object is to provide an improved graphite furnace characterized by a more advantageous flow path for protective gas to prevent combustion of the sample tube.

To the attainment of the foregoing and other objects and advantages which will become apparent as this description proceeds, the invention contemplates a graphite furnace in which the electrodes have hollow cylindrical portions which surround the sample tube along substantially its entire length but are radially spaced from the outer surface of the tube to define a hollow cylindrical clearance space around the tube.

Preferably, the confronting end faces of the electrodes cylindrical portions define a radially-stepped separating line space between them. In this manner, the graphite tube is completely shielded by the electrodes against radiation. Moreover, the separating line space constitutes a relatively long and narrow channel whose minimun cross-section does not change substantially with thermal expansion of the electrodes.

The hollow cylindrical electrode portions may have different lengths so that the separating line space is offset axially with respect to the sample port; the longer one of the electrodes cylindrical portion then has a radial bore aligned with the sample port.

There are provided means for introduction of a protective gas stream from both ends of the tube into the hollow body, this protective gas stream exiting through the sample port, at the mid-length region of the tube and discharge via an aligned radial bore in one of the electrodes. The electrodes surround the sample tube at a relatively small distance as compared with the cooling jackets and the housing parts of the prior constructions. Therefore, the radial bore in one electrode can have a relatively small diameter and still provide convenient access to the sample port for introduction of a sample, as by means of a pipette, for example.

The protective gas stream and the entrained particles of the atomized sample flow from the sample port in a sharp laminar flow jet which has no tendency to penetrate into the annular space between sample tube and electrodes. Therefore, this flow passes directly through the aligned radial bore in the one electrode.

BRIEF DESCRIPTION OF THE DRAWINGS

An exemplary embodiment of the invention will now be described more fully with reference to the accompanying drawings in which, FIG. 1 is a longitudinal sectional view of a flameless atomization apparatus according to the present invention taken along the axis of the sample tube and showing associated structure including electrodes, cooling jackets, and a mounting base;

FIG. 1A is an enlargement of the upper portion of FIG. 1;

FIG. 2 is a section on line 2—2 of FIG. 1 looking in the direction of the arrows;

FIG. 3 is an elevational view, partly in section, of the apparatus of FIG. 1 as seen from the right;

FIG. 4 is a plan view of the structure shown in FIG. 3;

FIGS. 5 and 6 are fragmentary sectional views taken on lines 5—5 and 6—6, respectively, on FIG. 4, looking in the direction of the arrows.

FIG. 7 is an axial sectional view of a sample tube constituting an alternative embodiment of the invention and including associated electrode structure;

FIG. 8 is an enlarged portion of FIG. 7 showing the contact between one end of the sample tube and the associated electrode; and FIG. 9 is a view similar to FIG. 8 showing a further modification of the invention.

DESCRIPTION OF THE PREFERRED EMBODIMENT

Referring now to the drawing and first in particular to FIG. 1, reference numeral 10 designates, in its entirety, a hollow body of electrically conductive material which defines a sample chamber and may herein be referred to as a sample tube. At substantially the mid-point of its length, tube 10 contains a radial bore 11 which provides a port for introducing the sample into the tube. As previously mentioned, tube 10, preferably, is fabricated of graphite and has conical end surfaces 12, 14 respectively. Respective electrode members 16, 18 comprise hollow cylindrical portions 20, 22 coaxially surrounding respective end portions of tubular body 10 and have annular end portions 24, 26 formed with conical surfaces complementary to and engaging end surfaces 12, 14 of tube 10.

Electrode members 16, 18 are mounted in respective cooling jackets 28, 30 each having a cylindrical recess 32, 34 for accommodation of the electrodes. Cooling jackets 28, 30 are fabricated of a material of high thermal and electrical conductivity and contain annular channels 36, 38 through which is circulated water or some other suitable coolant.

The outer cross-sectional dimension of cylindrical portions 20, 22 of electrode members 16, 18 is selected in relation to the internal cross-sectional dimension of recesses 32, 34 in cooling jackets 28, 30 so that, at room temperature, the electrode members fit snugly, i.e., can just be readily inserted into, the cooling jackets. In subsequent operation, when water or other coolant is circulated through channels 36 and 38, cooling the cooling jackets to below room temperation, they contract to create a positive contact pressure between the engaging cylindrical surfaces.

The contact pressure is increased during operation as a result of the heating and concomitant expansion of the electrode members by conduction of heat from graphite tube 10. Thus, heating of the electrodes acts to improve the contact between the mating surfaces in the same sense and manner as differences in thermal coefficients of expansion.

The internal surface of the hollow cylindrical portion of electrode members 16, 18 coact with the external surface of graphite tube 10 to form an annular space 40. In this connection, it will be noted that one of the electrodes, 16, is longer than the other and extends beyond the midpoint of the length of tube 10.

At a point coinciding with the midpoint of the length of tube 10, electrode member 16, contains a radial bore 39 in coaxial registration with, and of substantially larger diameter than bore 11.

The confronting inner ends of electrode hollow cylindrical portions 20, 22 are stepped so as to form a stepped annular groove 42 which, due to the greater length of electrode 16 is axially offset from center (to the right as viewed in FIG. 1).

Coaxial with cylindrical recesses 32, 34 and disposed outwardly of the annular ends of electrode members 16, 18, cooling jackets 28, 30 have stepped counterbores therethrough comprising respective smaller diameter segments 44, 46 adjoining said recesses and axially outwardly thereof, enlarged segments 48, 50.

Fitted into the counterbores of cooling jackets 28, 30 are hollow cylindrical inserts 52, 54 mounting respective radiation transparent windows 56, 58. Inserts 52, 54 are sealed in the counterbores by means of o-rings 60, 62 and can be axially withdrawn with the windows in place. Inserts 52, 54 are dimensioned so as to position windows 56, 58 symmetrically with respect to tube 10 so that the spaces formed at each end of the tube are of equal volume.

Passages (not shown) in the cooling jackets for supplying protective gas open tangentially in the smaller diameter segments 44, 46 of the counterbores as indicated by ports 64, 66. The gas is supplied via a connection 68 shown in FIG. 2.

The annular end portions 24, 26 of the cooling jackets are of conical configurations and coact with the walls of recesses 32, 34 to form annular spaces 70, 72 sealed with respect to counterbore segments 44, 46 by suitable packing strips (not shown).

Additional protective gas passages (also not shown but in communication with gas connection 68, FIG. 2) extend tangentially into spaces 70, 72 as indicated by ports 78, 80. Spaces 70, 72 in turn are connected, by way of three oblique ducts (82, FIG. 2) angularly-spaced at 120° in intervals about the axis of tube 10, with the ends of the annular space 40 surrounding the tube.

Cooling jacket 30 is spring-biased toward the adjoining end of tube 10 (i.e., to the left as viewed in FIG. 1). To this end, jacket 30 carries a cylindrical projection 84, coaxial with the tube 10 and the counterbore segments 46 and 50. Projection 84 is mounted in surrounding annular housing 86, by means of a pair of axially-spaced spring washers, 88, 90 of the type sometimes referred to as castle springs or Belleville springs, which are oriented to provide spring bias in the desired direction, i.e., inwardly toward tube 10.

Cooling jackets 28, 30 are coupled to a source of electrical power by means of connection terminals such as 92 and a copper cable 95 so that a high current may be conducted through the cooling jackets, the cylindrical mating surfaces of the jackets and electrode members 16, 18 to tube 10. The current path may include spring washers 88, 90 in which case, the power source is connected to housing member 86.

Figure 2:
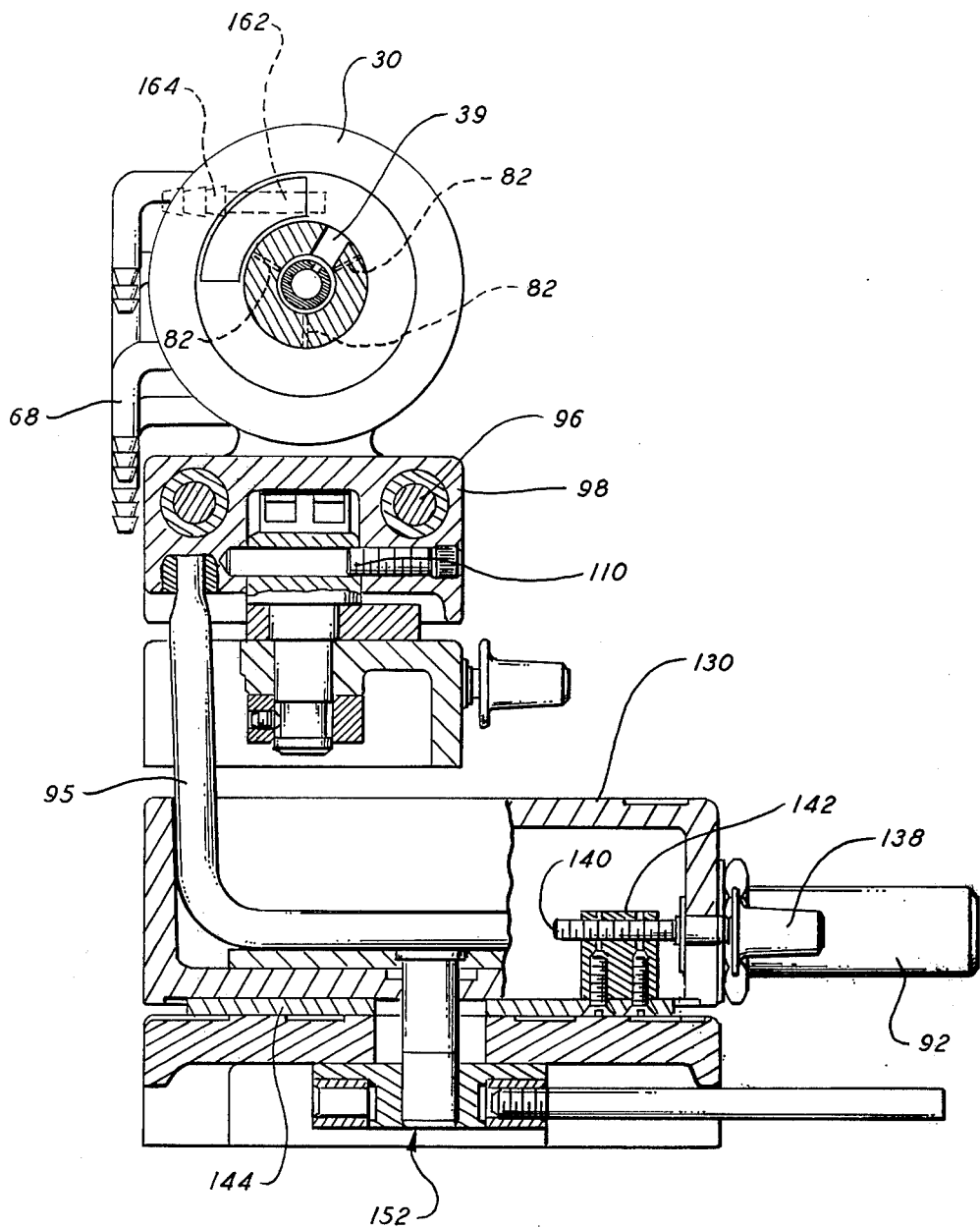

Cooling jacket 28 is secured to a pedestal 93 on which are mounted two substantially horizontal and parallel guide rods 94, 96 (FIG. 2). Slideably disposed on guide rods 94, 96 is the base 98 of annular housing member 86. The position of base 98 is locked with respect to guide rods 94, 96 by means of a lock member 100 which is vertically moveably guided on base 98 and has an aperture 102 through which guide rod 96 extends. Guide rod 96 has an annular groove in which the lock member engages under the influence of gravity, the aperture 102 then being eccentric to guide rod 96. Thus, base 98 is locked against displacement along rods 94, 96. Lock member 100 can be raised by means of a handle 104 and base 98 can then be withdrawn rightwardly (as viewed in FIG. 1); thus, the base and associated structure, viz., annular housing 86, cooling jacket 30, as well as electrode 18 can be removed from guide rods 94, 96, if necessary.

This construction permits a particularly simple installation (and removal) of graphite tube 10. When base 98 is withdrawn in the manner described, graphite tube 10 can be inserted into the left (longer) electrode member 16, the cylindrical portion 20 of which extends over more than half the length of the tube and surrounds it at a small radial distance. Tube 10 is then oriented about its axis so that its sample port 13 is correctly aligned with radial bore 39 of electrode 16. If base 98 is then moved leftwardly (as viewed in FIG. 1), the hollow cylindrical portion 22 of electrode 18 slips over the projecting right-hand end of tube 10, the tube centering with its conical end surfaces 12, 14 at the complementary conical contact surfaces of electrodes 16, 18. Graphite tube 10 is held between the conical surfaces of electrodes 16, 18 by an axial force applied by spring washers 88, 90. In contrast to prior graphite furnaces, no special tools are required for installation and removal of the sample tube.

Pedestal 93 and therewith base 98 are angularly adjustable to permit leveling of the horizontal axis of tube 10. To this and, a plate 107 having an integral pintle 108 is supported on a base plate 106 for rotation about a vertical axis defined by the pintle and extending through the axial midpoint of sample tube 10. Pedestal 93 is pivotally supported on pintle 108 by means of a horizontal pin 110 extending transversely through the pintle. A leaf spring 112 secured to the underside of pedestal 93 tends to pivot the pedestal about the axis of pin 110 in a counterclockwise direction (as viewed in FIG. 1). Under the influence of spring 112, the lower edge of pedestal 93 on the side remote from the spring abuts a linearly-moveable wedge 114 (FIG. 5) which is adjustable by means of an adjusting knob 116 and an adjusting spindle 118. In this manner, the inclination of graphite tube 10 about a transverse horizontal axis is precisely adjustable.

For adjustment about the vertical axis, plate 107 contains a slot 120. A pin 122 projects upwardly from a bearing member 124 and engages in slot 120. Bearing member 124 is constrained to linear movement and threaded on an adjusting spindle 126 which is rotatable by an adjusting knob 128 to vary the position of the bearing member.

Provision is made also to permit vertical adjustment of base plate 106 with respect to housing member 130. To this end, an adjusting spindle 134, rotatable by an adjusting knob 132 is guide in a nut 136 held in housing member 130.

Referring to FIG. 2, by means of an adjusting knob 138, an adjusting spindle 140, threaded in a block 142, is rotatably adjustable. Block 142 is located on a plate 144 slideably supporting housing member 130 so that, by rotation of knob 138, housing member 130 and therewith the graphite tube are adjustable transversely to the path of the radiation beam employed for atomic absorption analysis. Finally, plate 144 has on its underside guide keys 146 engaging in grooves 148 in a base member 150, thereby permitting translational movement of plate 144, and the parts mounted thereon, in a direction parallel to the path of the radiation beam, after release of a clamping device 152.

Reference numerals 92, 156 on FIG. 4 designate electrical connection terminals which are connected with flexible copper cables, one of which appears at 95 in FIG. 2. The copper cables conduct current to graphite tube 10 by way of the cooling jackets and electrode members.

In the graphite furnace of the invention, a radially-outwardly-open annular space 154 is formed around the mid-portion of tube 10 between the inner faces of cooling jackets 28, 30. The protective gas flow issuing through port 11 and bore 39 is substantially a laminar flow jet and is discharged from this annular space without significant contact with the adjoining walls of cooling jackets 28, 30.

In order to avoid contamination of the atmosphere, a suction device can be provided for annular space 154 as best appears in FIG. 2. This may consist of a piece of insulating material 160 mounted on electrode 16 and carrying a tube 162 terminating at one end closely adjacent to radial bore 39 and having a hose connection 164 on the other end for connection to a vacuum source.

In the case of conical contact surfaces between electrode members and the ends of the sample tube, differences in the electrical and thermal contact resistance may occur from tube to tube due to tolerances of the cone angles of the electrode members and of the ends surfaces of the tubes. These differences result in undesirable and uncontrolable temperature variation and temperature distribution from tube to tube. It has been determined that better-defined conditions are obtained if the graphite tube has planar end surfaces. Such planar end surfaces can be manufactured with sufficient accuracy to cooperate with a conical contact surface on the electrode members, a defined line contact being obtained. However, the conical contact surfaces of the electrode members may be provided with an annular shoulder having a cylindrical peripheral surface and a planer radial surface, the cylindrical surface surrounding the outer surface of the graphite tube with a predetermined clearance; the planer end face of the graphite tube abuts the radial surface of the shoulder.

Figure 8:
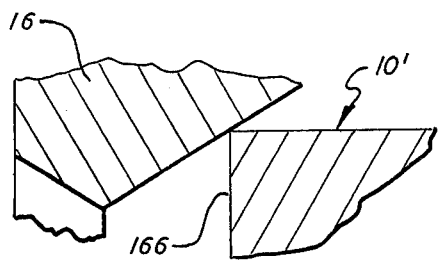
Figure 7:
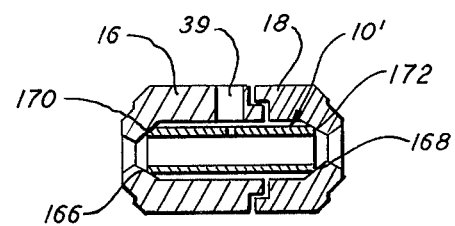

FIGS. 7 and 8 illustrate a graphite tube 10' having planar end surfaces 166, 168 which abut conical surfaces 170, 172 of electrodes 16, 18 with line contact.

Figure 9:
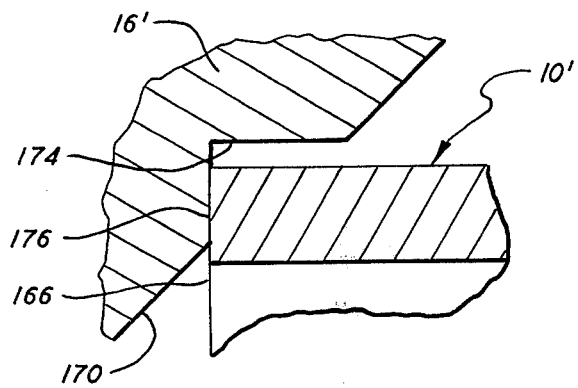
Figure 3:
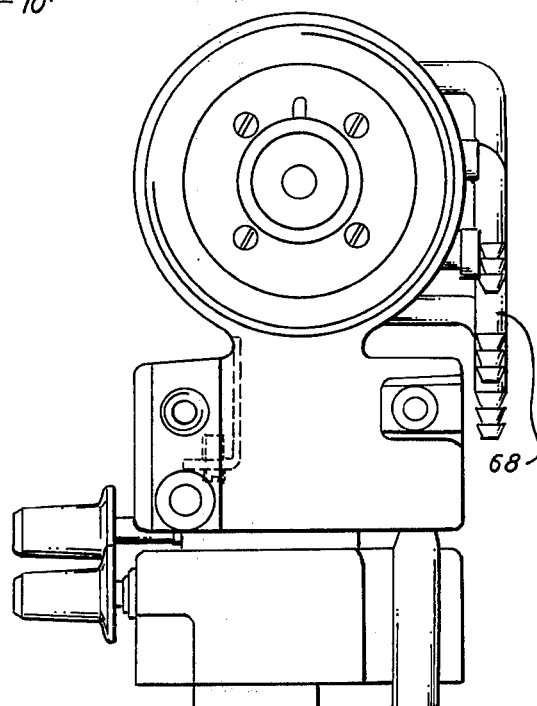
Figure 3:
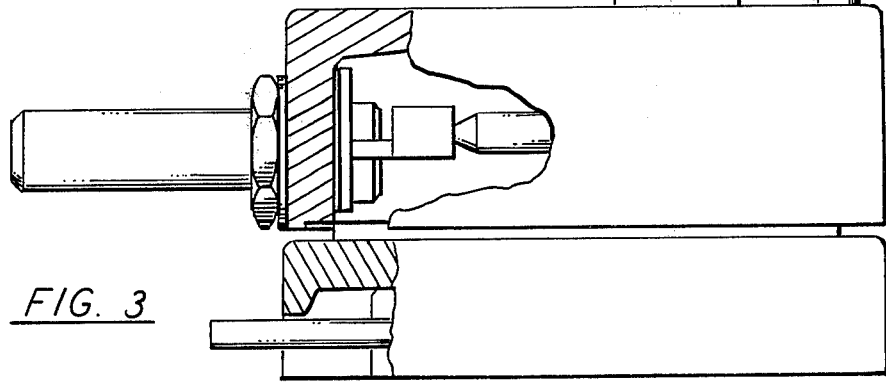

In the embodiment shown in FIG. 9, there is provided in conical surface 170 of electrode 16' an annular shoulder having a cylindrical peripheral surface 174 and a planer radial surface 176 in abuting engagement with the planer end 166 of graphite tube 10'. The described configuration of the contact between electrodes 16', 18' and graphite tube 10' are also advantageous inasmuch as only strictly axial forces act on the graphite tube.

From the foregoing description, it will be appreciated that the objects of the invention are attained in the provision of graphite furnace apparatus in which the introduction of a sample is facilitated as are the assembly, disassembly, and adjustment of the equipment. Concomitantly, parts on which deposits of atomized samples may collect are easily accessible for cleaning.

What is claimed is:

1. Apparatus for flameless atomization of a sample for atomic absorption analysis comprising:
   a. a hollow body of electrically conductive material defining a sample chamber having a radiation-transmissive passage therethrough; and
   b. electrode means including portions in electrical contact with said hollow body at spaced locations for passing an electrical current through the body to cause heating thereof and further including portions substantially enveloping and spaced from said hollow body and completely shielding said hollow body against radiation.

2. Apparatus for flameless atomization of a sample for atomic absorption analysis comprising:
   a. a sample tube of electrically conductive material;
   b. means defining a sample port in the sidewall of said tube at substantially the midpoint of its length;
   c. respective electrode members associated with each end of the sample tube, each comprising an annular portion in electrical contact with the respective end of the tube and a hollow cylindrical portion surrounding a respective portion of the length of the tube, the cylindrical portions of the electrode members jointly surrounding the tube along substantially its entire length at a distance from the exterior of the tube and coacting therewith to define a hollow cylindrical clearance space therebetween; and
   d. respective cooling jacket members having hollow cylindrical portions coaxially surrounding, and in heat conductive engagement with, the hollow cylindrical portions of the electrode members, said electrode members including means for completely shielding said cooling jackets means from said sample tube.

3. Apparatus according to claim 2 including:
   a. means for introducing a stream of protective gas into said tube from both ends thereof; the stream exiting through said sample port; and
   b. means defining an aperture in one of said electrode members in coaxial alignment with said sample port.

4. Apparatus according to claim 3 wherein the proximal ends of the electrode members ' hollow cylindrical portions have complementary, radially-stepped configurations defining a radially-stepped parting line space between them.

5. Apparatus acccording to claim 4 wherein the electrode member' hollow cylindrical portions have dissimilar axial dimensions thereby axially offsetting the parting line space with respect to the sample port, the longer of the electrode member cylindrical portions containing said aperture.

6. Apparatus according to claim 5 further comprising:
   a. conduit means for introducing said protective gas stream to the ends of said tube through the annular portions of said electrode members; and b. second conduit means for introducing a second protective gas stream entering from both ends of said clearance space between the electrode members' cylindrical portions and the sample tube and discharging partially through said electrode member aperture and partially between the radially-stepped parting line space.

7. Apparatus according to claim 6 wherein the first conduit means includes:
 a. means defining respective cylindrical chambers at each end of the sample tube coaxial therewith and spaced axially outward from the respective ends of the tube; and
 b. respective flow passage means opening tangentially into said cylindrical chambers.

8. Apparatus according to claim 7 wherein said electrode members and cooling jacket members coact to form respective annular chambers adjacent the ends of the tube and further comprising:
 a. means sealing said annular chambers from the respective cylindrical chambers of the first flow conduit;
 b. means defining respective flow passages opening tangentially into said annular chambers; and
 c. means defining flow channels in said electrode members extending between the respective annular chambers and the respective adjoining ends of said hollow cylindirical clearance space.

9. Apparatus according to claim 8 wherein the annular portions of the electrode members have external frusto-conical outwardly-facing surfaces coacting with the interior of said cooling jackets to define said annular chambers.

10. Apparatus according to claim 9 including respective groups of at least three passages symmetrically spaced about the axis of the sample tube and at each end of the tube placing the respectively adjoining one of said annular chambers in communication with the corresponding ends of said hollow cylindrical clearance space.

11. Apparatus according to claim 9 wherein said cooling jacket members have stepped bores extending therethrough in coaxial alignment with said hollow cylindrical portions thereof and said apparatus further comprises respective hollow insert members sealingly and removably fitted in the outer ends of said stepped bores, each insert member mounting a radiation transparent window transversely of and intersecting the axis of the sample tube.

12. Apparatus according to claim 9 wherein the annular portions of the electrode members have internal axially-inwardly facing surfaces in supportive engagement with the respective ends of the sample tube.

13. Apparatus for flameless atomization of a sample for atomic absorption analysis comprising:
 a. a sample tube of electrically conductive material;
 b. means defining a sample port in the sidewall of said tube at substantially the midpoint of its length;
 c. respective electrode members associated with each end of the sample tube, each comprising an annular portion in electrical contact with the respective end of the tube and a hollow cylindrical portion surrounding a respective portion of the length of the tube, the cylindrical portions of the electrode members jointly surrounding the tube along substantially its entire length at a distance from the exterior of the tube and coacting therewith to define a hollow cylindrical clearance space therebetween; and
 d. respective cooling jacket members having hollow cylindrical portions coaxially surrounding, and in heat conductive engagement with, the hollow cylindrical portions of the electrode members, said electrode members being mounted on and supported by said cooling jackets, and said apparatus further comprising:
 e. means for mounting one of said cooling jacket members for axial displacement toward and away from the respectively adjacent end of the sample tube; and
 f. means for resiliently biasing said one cooling jacket toward said adjacent end of the sample tube.

14. Apparatus according to claim 13 further comprising:
 a. guide rod means slideably supporting said mounting means for translational displacement along a path parallel to the axis of said sample tube; and
 b. releasable locking means for maintaining said mounting means at a predetermined position on said guide rod means, said mounting means being removable from said guide rod means upon release of said locking means and movement away from the sample tube.

15. Apparatus according to claim 14 further comprising:
 means for mounting said guide rod means and said other cooling jacket member for angular adjustment about respective horizontal and vertical axes transverse perpendicular to the axis of the sample tube at its midpoint.

16. Apparatus according to claim 15 further comprising:
 a. base plate means supporting said mounting means; and
 b. means supporting said base plate means for translational adjustment along two rectangular coordinates.

17. Apparatus according to claim 16 further comprising a suction device for applying suction to a region in close proximity to the aperture in said one electrode member.

18. Apparatus according to claim 2 wherein the annular portions of the electrode members have internal frusto-conical inwardly-facing surfaces in supportive engagement with the ends of said sample tube.

19. Apparatus according to claim 18 wherein the sample tube ends have frusto-conical surfaces complementary to said internal frusto-conical surfaces of the electrode members.

20. Apparatus according to claim 2 wherein the end faces of said sample tube lie in a plane perpendicular to its longitudinal axis.

21. Apparatus according to claim 18 wherein the end faces of said sample tube lie in a plane perpendicular to its longitudinal axis and the outer peripheral edges of said end faces make annular line contact with the frusto-conical inwardly-facing surfaces of the respective electrode members.

22. Apparatus according to claim 18 wherein the faces of said sample tube lie in a plane substantially perpendicular to its longitudinal axis and said apparatus further comprises means defining respective annular shoulders in said inwardly facing frusto-conical surfaces of the electrode members, said shoulders having cylindrical peripheral surfaces and annular radial surfaces complementary to and engaging the respective corresponding surfaces constituting the ends of the sample tube.

23. Apparatus for flameless atomization of a sample for atomic absorption analysis comprising:
   a. a sample tube of electrically conductive material;
   b. means for defining a sample port in the sidewall of said tube at substantially the midpoint of its length;
   c. respective electrode members associated with each end of the sample tube, each comprising an annular portion in electrical contact with the respective end of the tube and a hollow cylindrical portion surrounding a respective portion of the length of the tube, the cylindrical portions of the electrode members jointly surrounding the tube along substantially its entire length at a distance from the exterior of the tube and coacting therewith to define a hollow cylindrical clearance space therebetween, said electrode members having a configuration such that substantially no electrical current flow occurs through said cylindrical portions thereof; and
   d. respective cooling jacket members having hollow cylindrical portions coaxially surrounding, and in heat conductive engagement with, the hollow cylindrical portions of the electrode members.

* * * * *